United States Patent

Fonger et al.

[11] Patent Number: 5,190,528
[45] Date of Patent: Mar. 2, 1993

[54] PERCUTANEOUS TRANSSEPTAL LEFT ATRIAL CANNULATION SYSTEM

[75] Inventors: James D. Fonger, Wayland, Mass.; Kenneth R. Jonkman, Grand Rapids, Mich.; James H. Anderson, Columbia; Sally E. Mitchell, Baltimore, both of Md.

[73] Assignee: Boston University, Boston, Mass.

[21] Appl. No.: 600,483

[22] Filed: Oct. 19, 1990

[51] Int. Cl.$^5$ .............................................. A61M 5/00
[52] U.S. Cl. .................................. 604/171; 604/164; 604/281; 604/284; 128/658
[58] Field of Search ............... 604/158, 161, 164, 165, 604/166, 167, 168, 169, 170, 171, 280, 281, 282, 284; 128/656, 657, 658

[56] References Cited

U.S. PATENT DOCUMENTS

| | | | |
|---|---|---|---|
| 4,306,562 | 12/1981 | Osborne | 604/280 |
| 4,405,314 | 9/1983 | Cope | 604/170 |
| 4,581,025 | 4/1986 | Timmermans | 604/164 |
| 4,596,559 | 6/1986 | Fleischhacker | 604/170 |
| 4,650,472 | 3/1987 | Bates | 604/165 |
| 4,668,221 | 5/1987 | Luther | 604/166 |
| 4,738,666 | 4/1988 | Fuqua | 604/280 |
| 4,787,884 | 11/1988 | Goldberg | 604/170 |
| 4,790,825 | 12/1988 | Bernstein et al. | 604/170 |
| 4,874,360 | 10/1989 | Goldberg et al. | 604/281 |
| 4,895,564 | 1/1990 | Farrell | 604/164 |
| 4,898,577 | 2/1990 | Badger et al. | 604/282 |
| 4,935,008 | 6/1990 | Lewis, Jr. | 604/164 |
| 4,983,169 | 1/1991 | Furukawa | 604/164 |
| 4,986,814 | 1/1991 | Burney et al. | 604/164 |
| 4,988,356 | 1/1991 | Crittenden et al. | 128/658 |

FOREIGN PATENT DOCUMENTS

| | | | |
|---|---|---|---|
| 0161636 | 11/1985 | European Pat. Off. | 604/164 |
| 91/07710 | 10/1991 | PCT Int'l Appl. | |
| 88/02875 | 8/1988 | World Int. Prop. O. | |

OTHER PUBLICATIONS

Clarence Dennis et al, "Clinical Use of a Cannula for Left Heart Bypass Without Thoracotomy: Experimental Protection Against Fibrillation by Left Heart Bypass," *Annals of Surgery*, vol. 156, No. 4, pp. 623-637, Oct. 1962.

(List continued on next page.)

Primary Examiner—Gene Mancene
Assistant Examiner—Frank A. LaViola
Attorney, Agent, or Firm—Hamilton, Brook, Smith & Reynolds

[57] ABSTRACT

A transseptal left atrial cannulation system which provides drainage of left atrial blood without the need for thoracotomy. A guide wire and a long needle assembly are inserted into a catheter. A cannula rides over the exterior of this catheter. The guide wire may be advanced past the needle assembly and through a catheter through the distal end of the catheter to assist in directing the system to the right atrium. The cannulation system is inserted in a femoral vein located in the groin. Both the guide wire and needle assembly are long enough to allow a substantial length to extend out of the body at the groin for manipulation even when the distal ends of the guide wire and needle assembly are positioned in the heart. When the catheter distal end is positioned adjacent the septum in the right atrium, the guide wire is withdrawn from the catheter orifice and the needle assembly moves past the guide wire and through the catheter orifice to a position adjacent to the septum. The needle pierces the septum and the catheter moves over the needle assembly to further dilate the septal hole. The cannula attached to the catheter also moves through the septal hole, further dilating it, and resting with the holes in the left atrium. The guide wire, the needle assembly, and the catheter are withdrawn from the cannula. Oxygenated blood from the left atrium drains through the cannula to the extracorporeal pump and back to the body through an arterial cannula.

42 Claims, 7 Drawing Sheets

OTHER PUBLICATIONS

"A method of closed-chest cannulation of the left atrium for left atrium for left atrial-femoral artery bypass", Glassman et al., *The Journal of Thoracic and Cardiovascular Surgery*, vol. 69, No. 2, pp. 283–290, Feb. 1975.

"Left Atrial Cannulation without Thoracotomy for Total Left Heart Bypass", Dennis, et al., *ACTA Chir Scand*, vol. 123, pp. 267–279, (1962).

"Percutaneous Assist Device Provides Simple Technique for Total Left Ventricular Support", Grossi et al., *Surgical Forum*, American College of Surgeons, 1985.

"Use of Percutaneous Left Ventricular Assist Device Provides A Simple Means For Reduction of Infarct Size During Reperfusion of Evolving MI", Grossi et al., Abstracts Circulation, vol. 72, Supp III, Oct., 1985.

"Closed-chest left heart bypass without anticoagulation", Wakabayashi, et al., *Journal of Thoracic and Cardiovascular Surgery*, vol. 58, No. 6, Dec., 1969, pp. 811–820.

PERCUTANEOUS TRANSSEPTAL LEFT ATRIAL CANNULATION SYSTEM

BACKGROUND

Circulatory support during coronary bypass surgery, heart transplantation, or after failed coronary angioplasty is currently achieved using cardiopulmonary bypass. This involves the complete support of the heart and lungs by diverting all the blood returning to the heart through a pump and oxygenator, before returning it to the arterial circulation. During coronary artery bypass grafting or heart transplantation, cannulation for cardiopulmonary bypass is done at surgery through the chest, whereas cardiopulmonary bypass for failed coronary angioplasty can be done percutaneously through the groin in the cardiac catherization lab. Regardless of the circumstances or route of cannulation, cardiopulmonary bypass has a time limitation of three to four hours due to the continued trauma to formed blood elements such as platelets and red blood cells. This is primarily due to the oxygenator in the circuit. The patient must undergo full anticoagulation with heparin prior to cardiopulmonary bypass and the bypass circuit must be assembled and run by a certified perfusionist.

Circulatory support before and after surgery may be required for several days. Usually the lungs and right ventricle are functioning adequately and only the left ventricle requires extended support. The employment of left ventricular assist allows extended circulatory support without the blood trauma of cardiopulmonary bypass or the services of a perfusionist and requires only partial anticoagulation.

Left ventricular assist requires the drainage of blood from the left atrium of the heart which is currently done by cannulation of the left atrium at the time of surgery. In 1962, an alternative method called "transseptal left atrial cannulation" was proposed by Dennis et al.. in "Left Atrial Cannulation without Thoracotomy for Total Left Heart Bypass", *Aca. Chir. Scand.* 123: 267–279, 1962 using a metal cannula directed down the right jugular vein. The cannula was directed across the interatrial septum and drained left atrial blood without the need for thoracotomy. More recently, Glassman et al. in "A method of closed-chest cannulation of the left atrium for left atrial-femoral artery bypass", *The Journal of Thoracic and Cardiovascular Surgery*, Vol. 69, No. 2, February 1975 has advocated transseptal left atrial cannulation by the right femoral vein. These publications describe hardware and procedures which are too complex and awkward for widespread clinical acceptance.

U.S. Pat. No. 4,790,825 issued to Bernstein et al. illustrates one proposed method of transseptal left atrial cannulation based largely on work with the Glassman group. In Bernstein, first a guide wire protruding through a catheter is inserted into the femoral vein and directs the catheter up the veins to the right atrium. Second, the guide wire is withdrawn from the entire length of the catheter and a needle is directed up the entire length of the catheter and protrudes out the end. The needle pierces the interatrial septum and the catheter is advanced over the needle into the left atrium. Third, the needle is removed from the entire length of the catheter and an obturator (with a circular barb for attaching to the catheter hub) is directed up the entire length of the catheter. Fourth, an external obturator extension is screwed on to the internal obturator. Fifth, a cannula is threaded over the entire length of the catheter and obturator with the tip positioned in the left atrium. Finally, the catheter and the obturator are removed from the interior of the cannula. A thoracotomy is not required for insertion or removal of the left atrial cannula.

SUMMARY OF THE INVENTION

The cannulation method of Bernstein is complex. The insertion and removal of the guide wire, the needle, and obturator within the catheter risks potential system movement, dislodgement, inadvertent puncturing of chamber walls, and may compromise system sterility. Valuable time is wasted during the required insertions and removals. Also, if the internal obturator circular barb should malfunction, the catheter cannot be removed from within the cannula. Accordingly, a simpler, quicker, and safer technique for transseptal left atrial cannulation is desirable.

The invention comprises a method and device for draining blood from the left atrium of the heart by utilizing a cannula and catheter in which a guide wire and a needle assembly are positioned axially. The guide wire and the needle assembly can be extended alternately through the distal catheter orifice. A cannula is positioned over the catheter (and can slide thereover) and is inserted into a blood vessel with the catheter. This axial configuration of all the system elements obviates the need for repeated insertion and withdrawal of the guide wire and the needle. Both the guide wire and needle are initially and throughout the procedure positioned within the catheter close to the catheter orifice and can be alternately advanced. The cannula is also initially moved through the veins with the catheter. Once the cannula has been advanced into the left atrium, the guide wire, needle assembly and the catheter can be easily withdrawn in an integral fashion without the risk of barb malfunction leaving the catheter behind. Thus, left drainage can be accomplished safely, quickly, and without compromising sterility.

The device is used as the venous cannula in a percutaneous transseptal left atrial cannulation system for a left ventricular assist. In use, the catheter, guide wire, needle assembly, and cannula are coaxially configured and inserted together. The device is inserted into the femoral vein in the groin, the guide wire is extended through the distal catheter orifice, and under fluoroscopic guidance, the guide wire followed by the catheter, needle, and cannula are positioned in the right atrium of the heart. Both the guide wire and needle assembly are long enough to allow a substantial length to extend out of the body at the groin for manipulation even when the distal ends of the guide wire and needle assembly are positioned in the heart. The guide wire is withdrawn into the catheter and remains within the catheter body. The needle assembly is advanced through the catheter orifice to the septum and pierces a hole through the septum into the left atrium. The needle assembly is stiff enough to permit the catheter to advance over it through the septum and into the left atrium. The cannula is then advanced over the catheter through the septum into the left atrium. (Conventional, off the shelf interatrial septal needles are too short and flexible. For example, the conventional Ross and Brockenbrough needles would not be stiff enough to allow the cannula to ride thereover when the needle is positioned in the heart and would not be long enough to allow manipulation through a catheter/cannula coupling assembly.) The guide wire, needle assembly, and catheter are removed as an integral unit, leaving only the cannula with its tip in the left atrium. Oxygenated blood from the left atrium of the heart is drained by this venous cannula and is returned to the body by an arterial cannula after passing through an extra-corporeal pump. Thus, left ventricular assist is accomplished without the need for thoracotomy.

This technique is simple, safe, efficient and inexpensive. Insertion and removal of individual system elements is avoided and the surgical procedure of thoracotomy is not required for placement or removal. The time restrictions of conventional cardiopulmonary bypass are removed and full patient anticoagulation is not required for this simple extra-corporeal assist circuit. A certified perfusionist is not required to set up or run this system and the cannulae connect to a simple centrifugal pump which is already available as conventional hospital equipment.

The preferred invention includes a peel-away sheath assembly comprised of a thin-walled tube with a tapered end which covers a plurality of holes on the side of the end of the cannula. A hub is molded onto the thin-walled tube. The hub and tube are scored so that they can be pulled back from the cannula and peeled away. During the initial stage of insertion of the system into the femoral vein, the sheath prevents the cannula holes from accumulating particulate fat debris prior to reaching the blood stream. The sheath is pulled back and peeled away after the cannula is within the femoral vein. This ensures no debris will reach the left atrium and possibly cause a stroke.

In the preferred embodiment, the cannula is coated on both sides with an anti-thrombogenic coating to minimize the potential for blood coagulation on the cannula during long term use.

In the preferred embodiment, the needle assembly includes a metal tube with a narrowed distal end such that a predetermined length of tube can extend out of the catheter orifice but a thicker tube width is stopped at the orifice. The metal tube comprises an inner metal tube which is fixed coaxially within but extends beyond a second outer metal tube. The inner tube has a distal end which is rounded to prevent scraping within the catheter. The inner tube is small enough to pass through the catheter orifice, whereas the outer tube cannot. Thus, the inner tube protrudes only a fixed safe distance from the catheter orifice. A needle wire can be positioned within the inner tube and can be advanced a fixed distance out the distal end of the tube to sharpen the needle. The inner needle lumen also allows aspiration of blood to confirm correct left atrial positioning. The needle assembly is stiff enough to also function as the obturator which holds the catheter rigid during cannula advancement.

The distal end of the needle assembly can be molded into a curve by the operator to assist in directing the needle across the septum. However, under single plane fluoroscopic guidance the needle direction cannot be accurately determined from the screen alone. To confirm the spatial orientation of the curved end of the needle, a hub with a pointer is connected to the proximal end of the needle assembly.

The above and other features of the invention including various novel details of construction and combinations of parts will now be more particularly described with reference to the accompanying drawings and pointed out in the claims. It will be understood that the particular device embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIGS. 5(a), (b), and (c) illustrate a detailed longitudinal cross-sectional view of the distal assembly with different positions of the guide wire, needle and needle wire.

DETAILED DESCRIPTION OF THE PREFERRED EMBODIMENTS

Figure 1A:
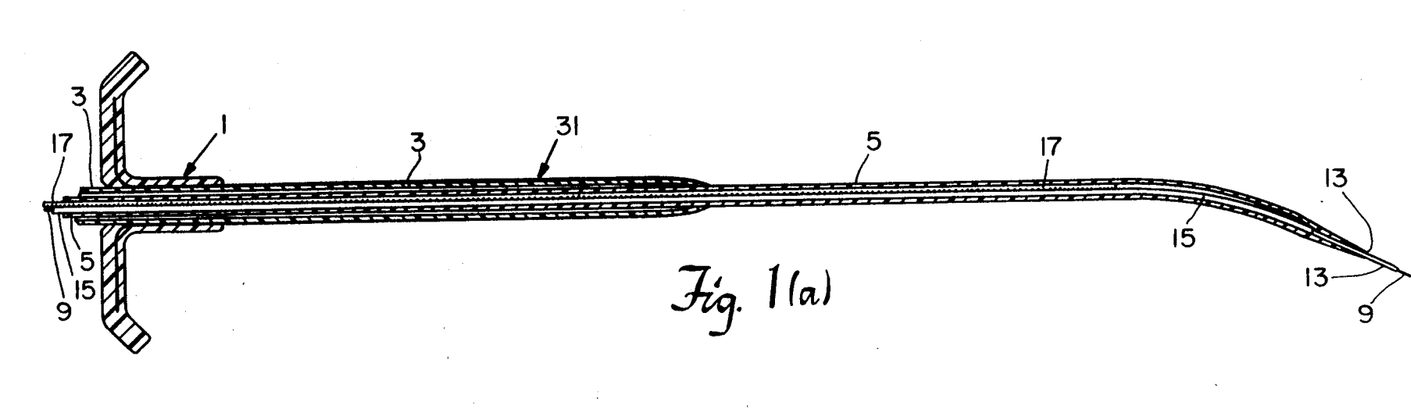
FIG. 1(a) illustrates a longitudinal cross-sectional view of the distal end of the cannulation system.
Figure 1B:
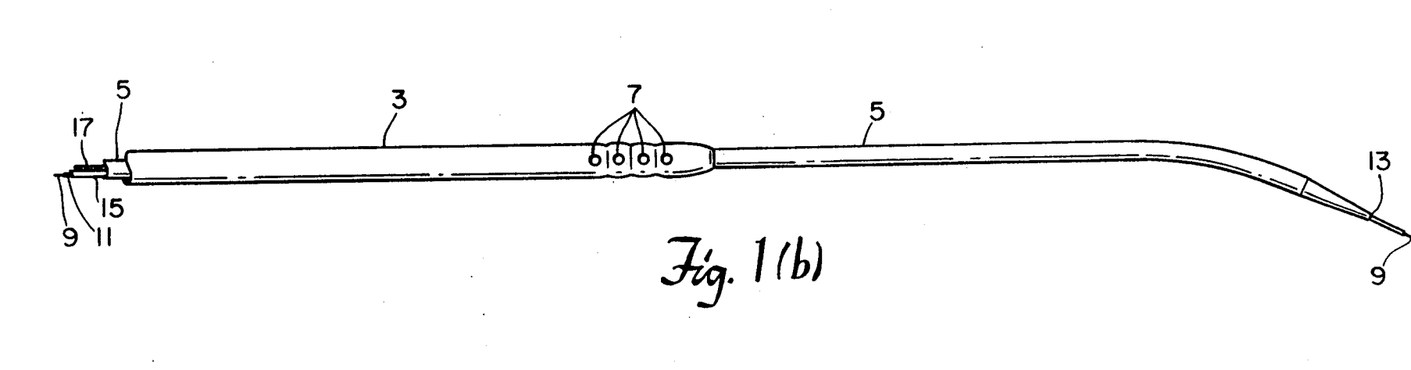
FIG. 1(b) shows a side view of the distal end of the cannulation system.
Figure 4A:
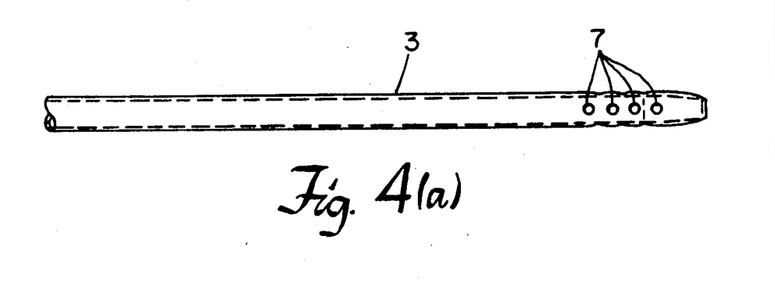
FIG. 4(a) shows the cannula distal end.
Figure 4B:
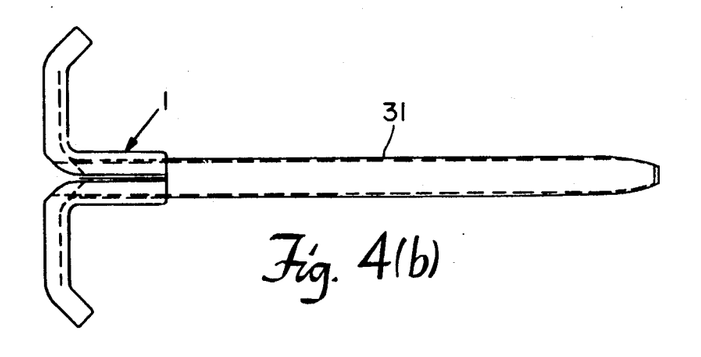
FIG. 4(b) illustrates the peel-away sheath assembly.
Figure 4C:
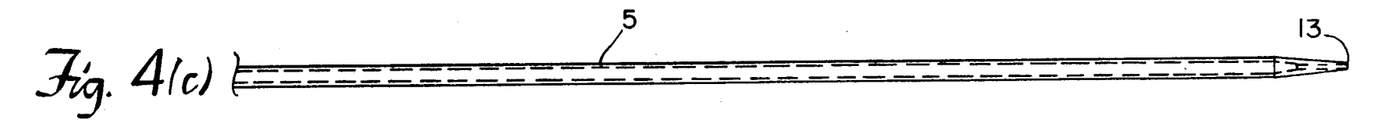
FIG. 4(c) shows the catheter distal end.

FIGS. 1(a) and (b) illustrate the distal end of the cannulation system. A radio-opaque polyurethane catheter 5 comprising a 32 inch long (but can vary in range from 30 inches to 35 inches), 12 french tube contains a guide wire 17 and a needle assembly 9, 11, 15 which can alternately be advanced through the orifice 13 as shown in FIG. 4(c) in the catheter distal end. The catheter is not preformed, but the assembly can be bent by the physician prior to insertion, and the needle retains the shape and imparts a shape to the catheter as illustrated. The needle has sufficient shape memory, yet is sufficiently flexible to follow the shape of a vein without losing its curve once it moves into the atrium.

Figure 4D:
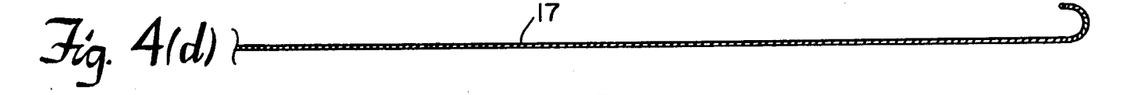
FIG. 4(d) shows the guide wire distal end.
Figure 4E:
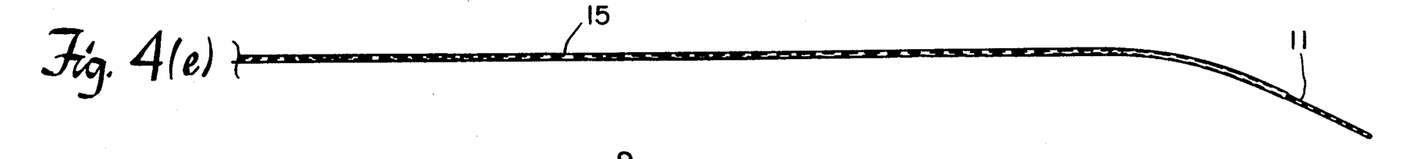
FIG. 4(e) shows the needle assembly distal end.
Figure 4F:
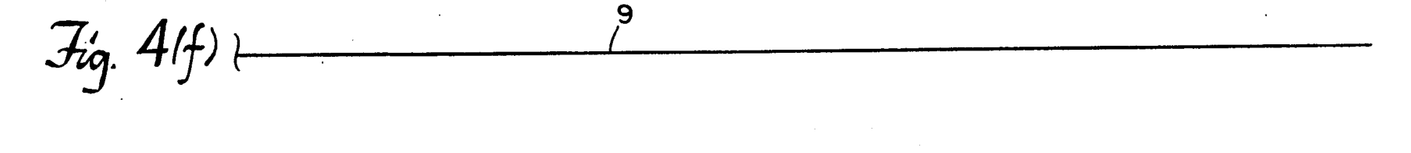
FIG. 4(f) shows the needle wire distal end.

As shown in detail in FIGS. 4(e) and (f) the needle assembly includes a needle wire 9 which is stainless steel, a first metal tube 11 which can advance through the catheter orifice 13 and an outer metal tube 15 which cannot extend through the catheter orifice 13. A single metal tube with a narrowed distal end such that a predetermined length of tube projects out of the catheter orifice but a thicker tube width is stopped at the orifice may be substituted for tubes 11 and 15. The needle assembly comprises two pieces of hypodermic stainless steel tubing of No. 3. temper, held together coaxially by a molded PETG copolyester hub 29. The 20 gauge outer diameter of the smaller tube is 0.75 inches longer than the 37 inch long, 18 gauge larger tube. The stainless steel needle wire 9 is 39 inches long and 0.015 inches in diameter. (The lengths of the needle assembly components can be shortened by 2 inches or lengthened by 3 inches. The lengths can be any dimension within this range.) The outer tube 15 has a wall thickness of 0.006 inch, an outer diameter range of 0.0495 inch–0.0505 inch and an inner diameter range of 0.0375 inch–0.0395 inch. The inner tube 11 has a wall thickness of 0.006 inch, an outer diameter range of 0.0355 inch–0.0360 inch and an inner diameter range of 0.0230 inch–0.0245 inch. The smaller inner metal tube fits inside of the outer metal tube. The smaller tube is than the outer tube and protrudes out the end for a fixed distance and has a rounded end to prevent scraping within the catheter 5. At the catheter tapered tip, the inner diameter is reduced to 0.036 inch so that only the 0.036 inch guide wire or only the 20 gauge needle can fit through the orifice 13. The outer tube 15 cannot fit through the catheter orifice 13 and fixes the distance which the inner tube 11 can extend beyond the catheter orifice 13.

The needle assembly punctures the septum and subsequently acts as a stiff curved guide to direct both the catheter and cannula across the septum and into the left atrium. The needle assembly has a stiffness sufficient to guide the catheter and cannula over it as well as have adequate flexibility to permit passage through the veins enroute to the right atrium. Hypodermic needle stock full hard at the aforementioned gauges is used to satisfy the stiffness requirements.

The cannula 3 consists of a 24 inch (but can vary in range from 22 inches to 27 inches) long 21 french radiopaque thin wall polyurethane tube with a tapered tip and side holes 7 at its distal end. The outer diameter for cannula 3 with a 21 french tube is 0.276 inch. The cannula 3 tube size can vary from 18 french to 24 french. The cannula tapered tip slides over the exterior of catheter 5. The catheter 5 has an inner diameter of 0.100 inch and the cannula 3 has an inner diameter of 0.216 inch. The cannula is coated on both sides with an antithrombogenic agent. For example, the cannula may be typically bonded with heparin.

A peel-away sheath assembly is comprised of polypropylene hub 1 which is molded onto a 5 inch long thin-walled polytetrafluorethylene tube 31 with a tapered end. Both the hub and the tube are scored in such a way that they will tear longitudinally in half and be easily removed from the cannula. The peel-away sheath covers the holes 7 in the cannula 3 during the initial stage of percutaneous insertion when the cannula traverses the subcutaneous fat. It shields the cannula holes from accumulating particulate subcutaneous fat debris prior to reaching the blood stream. Once the cannula is within the femoral vein, the sheath is pulled back and peeled away. FIGS. 4(a) and 4(b) show the cannula and the peel-away sheath assembly in more detail.

Figure 2A:
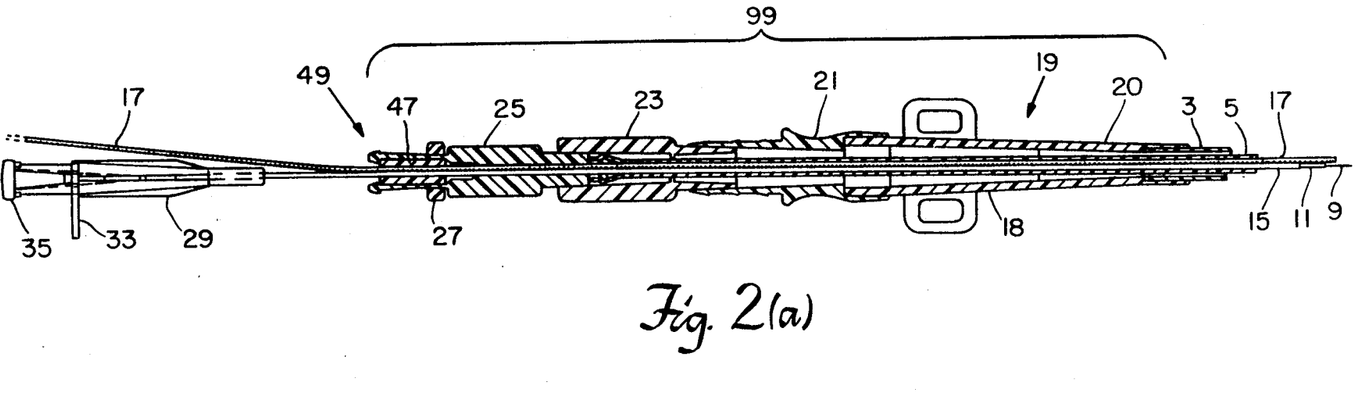
FIG. 2(a) illustrates a longitudinal cross-sectional view of the proximal end of the cannulation system.
Figure 2B:
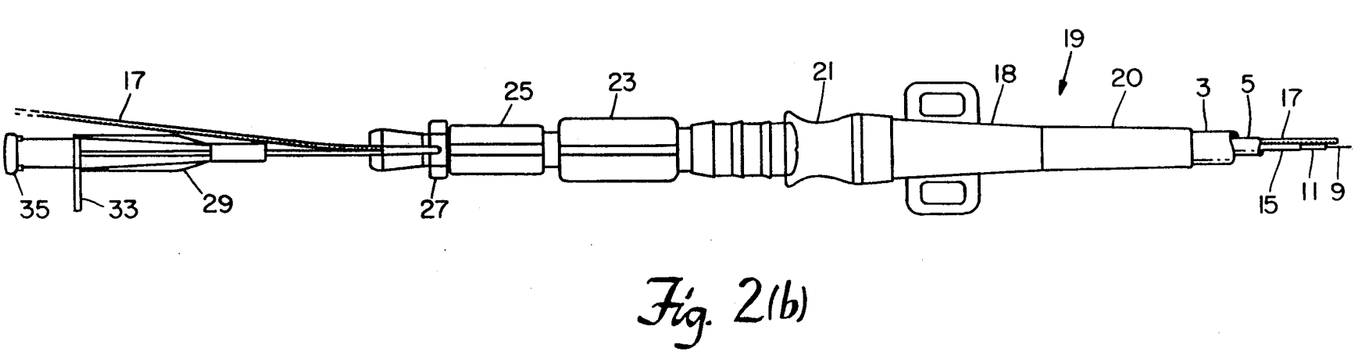
FIG. 2(b) shows a side view of the proximal end of the cannulation system.
Figure 3A:
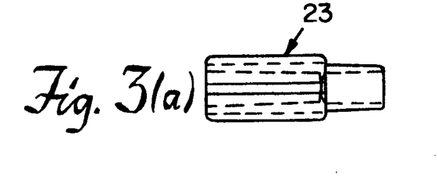
FIG. 3(a) shows a reducer plug in the system of FIG. 2(b).
Figure 3B:
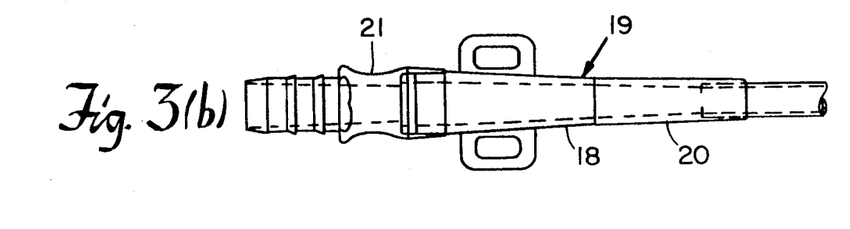
FIG. 3(b) illustrates a cannula hub in the system of FIG. 2(b).
Figures 3C, 3D:
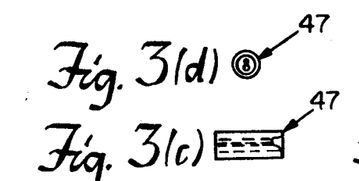
FIGS. 3(c) and 3(d) illustrate side and transverse end views, respectively, of the dual lumen elastic bushing of FIG. 2(b).
Figure 3E:
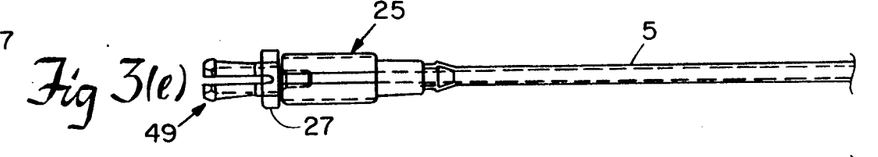
FIG. 3(e) shows a side view of the proximal end of the catheter.
Figures 3F, 3G, 3H, 3I:
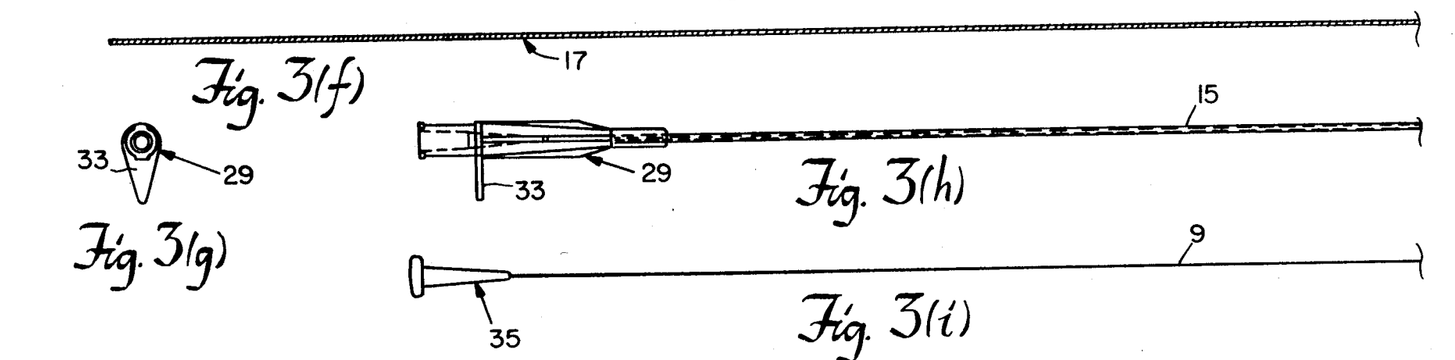
FIG. 3(f) shows the proximal end of the guide wire.
FIG. 3(g) illustrates a transverse end view of the hub and pointer of the needle assembly proximal end.
FIG. 3(h) shows a longitudinal view of the needle assembly proximal end.
FIG. 3(i) shows a longitudinal view of the needle wire proximal end.

FIGS. 2(a) and (b) show the cannulation system proximal end. The catheter-cannula coupling assembly 99 is comprised of cannula hub 19, barb tube connector 21, reducer plug 23, male connector 25, bushing holder 49, bushing 47 and closing ring 27. The cannula hub 19 is clear, hollow, and comprised of two polyvinylchloride components 18 and 20. The distal component 20 of hub 19 is flexible and can be clamped. As shown in FIG. 3(b), the cannula hub 19 distal end is fixed to the cannula 3. The cannula hub 19 proximal end is rigid and fixed to a rigid, barbed tube connector 21 which has a standard ⅜ inch diameter. A reducer plug 23, shown in detail in FIG. 3(a), includes a molded polypropylene male tapered connector on its distal end and a female tapered connector on the proximal end. The reducer plug male connector is attached to the tube connector 21. The tube connector 21 is comprised of a proximal component which is attached to the inner portion of a distal component. The reducer plug female connector wraps around the proximal catheter end to minimize blood loss. As shown in FIGS. 3(c), (d), and (e), the catheter proximal end includes a polypropylene male connector 25 with a bushing holder 49 including jaws, a dual lumen elastic silicone bushing 47, and a closing ring 27 which provides a friction fit to prevent the guide wire and needle assembly from moving if fixation is desired. The guide wire and the needle assembly are alternately moved axially within the catheter. When properly located, their respective positions are fixed by means of closing ring 27 which clamps both elements.

As shown in FIGS. 3 (g), (h), and (i), the needle assembly proximal end includes a hub 29 attached to the metal tubes, a pointer 33 for indicating the angular orientation of the curved distal end of the needle assembly, and a molded polypropylene hub 35 attached to the needle wire 9. A single plane fluoroscopic display cannot distinguish the anterior or posterior position of the curved needle distal end. However, when display information is combined with the pointer indication, the needle orientation can be determined. Moreover, the integral configuration of the system allows the protected delivery of the needle assembly to the right atrium of the heart over the guide wire. The guide wire 17 is pulled back and the needle wire 9 and the inner metal tube 11 are advanced to effect the transseptal puncture of the heart. FIG. 3(f) shows the guide wire proximal end which is moved to position the guide wire. The guide wire 17 is comprised of a stainless steel spring wire wrapped around a separate core wire. The guide wire 17 is 140 cm long and 0.036 inch in diameter. The distal end of the wire is more flexible than the center portion. The guide wire is preformed and has hysteresis to assume a curved shape when extended out of the catheter to prevent catching of the wire on venous side branches, as shown by FIG. 4(d). The guide wire guides the catheter to the right atrium and once the catheter is in the left atrium it can be used to assess the distance to the lateral left atrial wall. It can also be used to deflect and foreshorten the catheter tip to minimize the risk of damaging the wall of the left atrium after the catheter has advanced through the septum.

Figures 5A, 5B, 5C:
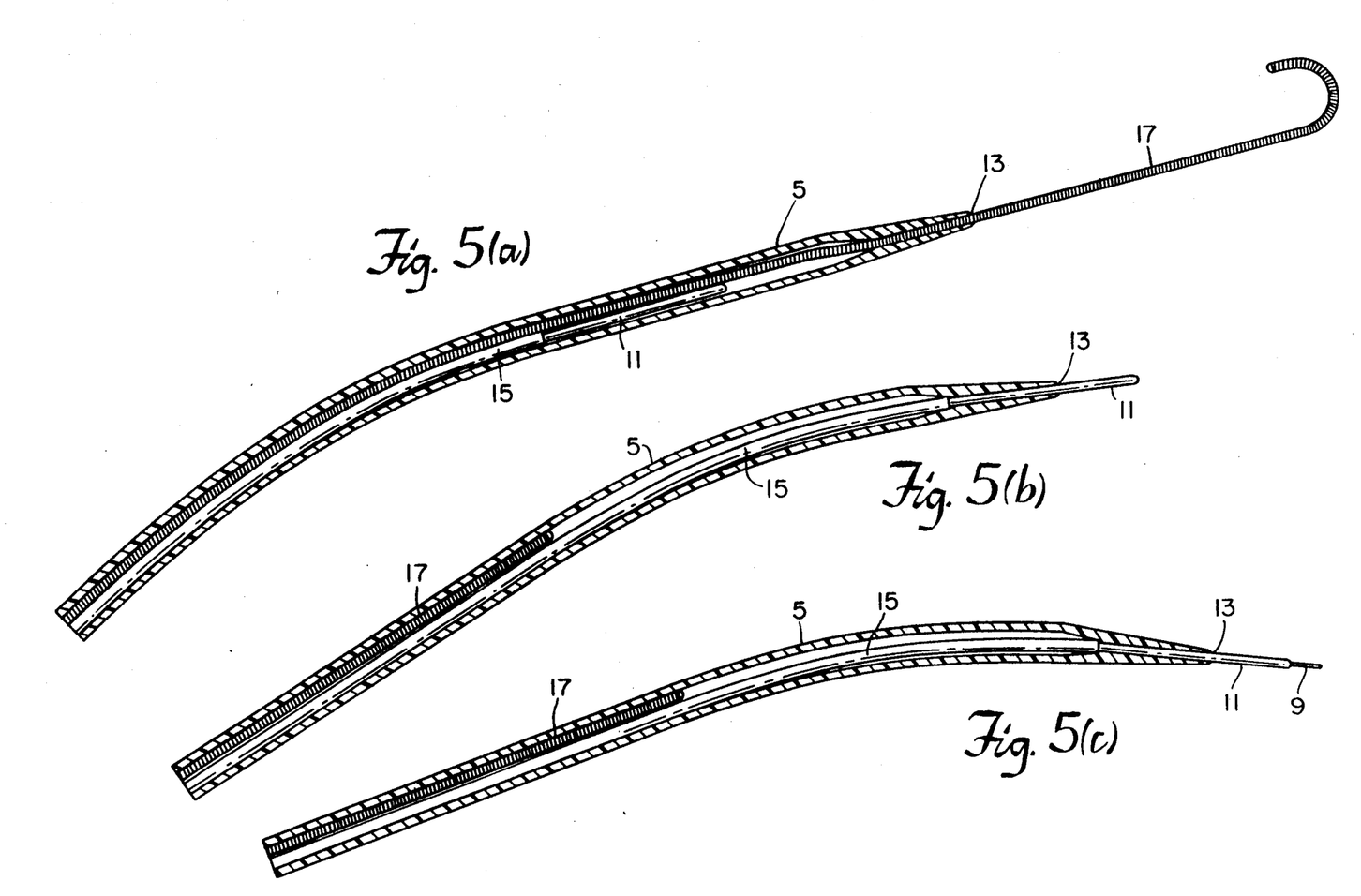

FIGS. 5(a), (b) and (c) illustrate the operation of the catheter elements. The catheter curvature results from conforming to the preformed needle curve. FIG. 5(a) shows guide wire 17 extended in a curled configuration to facilitate guiding the catheter through the venous system. FIG. 5(b) shows the withdrawn guide wire and extended inner metal tube 11 of the needle assembly. FIG. 5(c) shows the needle wire 9 extended through the inner metal tube 11 to sharpen the needle assembly.

Figure 6A:
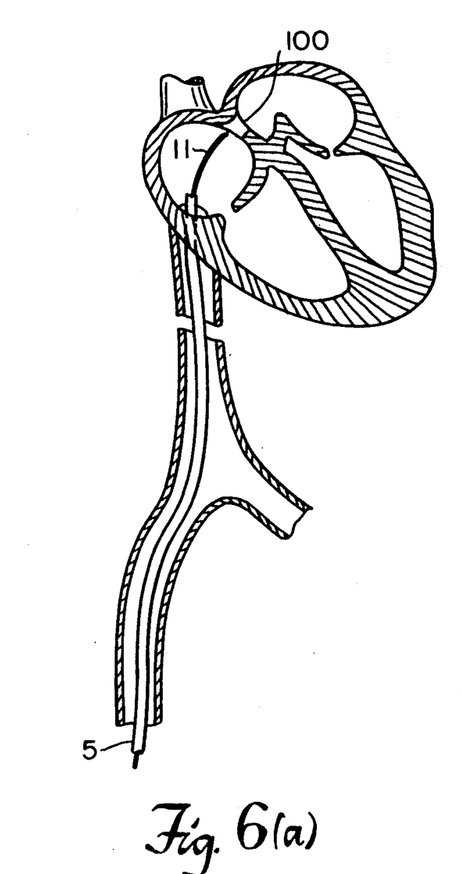
FIGS. 6(a), (b), and (c) show the progressive placement of the cannulation system into the heart.
Figure 6B:
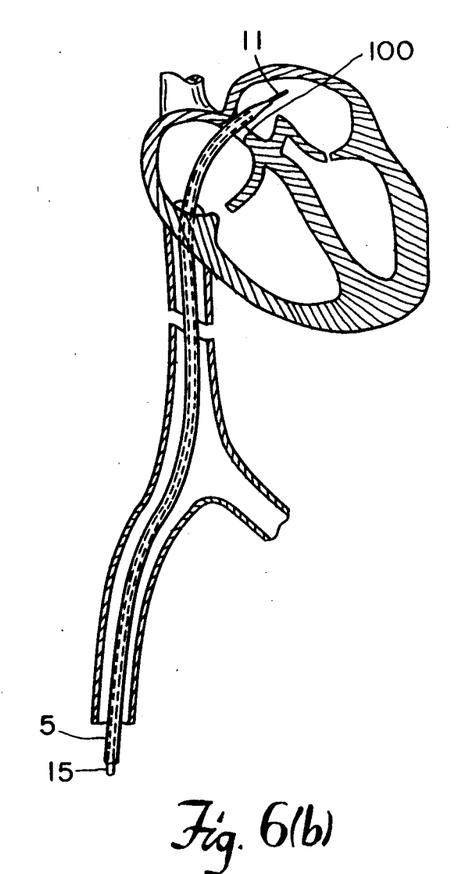
Figure 6C:
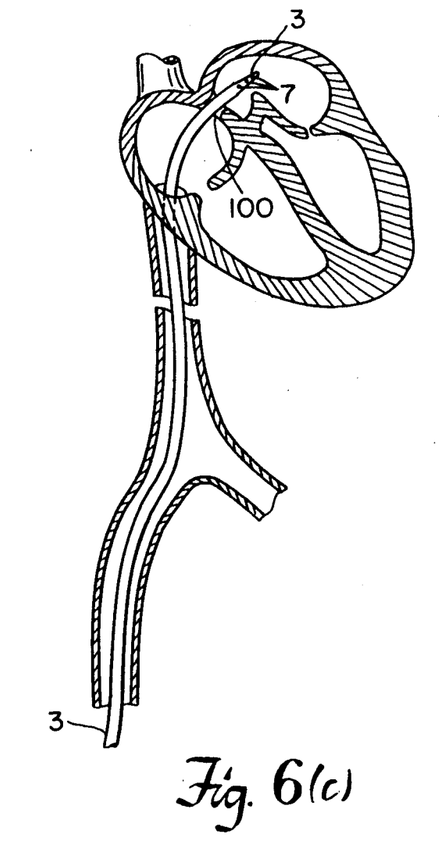

FIGS. 6(a), (b), (c) illustrate the steps in positioning of the inventive system in the heart. The cannulation system is inserted into the femoral vein using a conventional breakaway Seldinger needle through which guide wire 17 is threaded. The transseptal cannulation system is advanced over guide wire 17 into the femoral vein. Both the guide wire and needle are long enough to allow a substantial length to extend out of the body at the groin for manipulation even when the distal ends of the guide wire and needle are positioned in the heart. Thus, the cannula can be easily loaded thereover and carried therewith through the vein. Once the cannula holes 7 pass into the blood stream, the sheath 1, 31 is pulled back and peeled away. The guide wire 17 assists in guiding the cannulation system to the right atrium of the heart under fluoroscopic guidance. Once the catheter is in the right atrium with the cannula at the level of the diaphragm, the guide wire is withdrawn into the catheter and the needle assembly is advanced to the septum. FIG. 6(a) shows this position where the curved end of the needle-catheter is touching the septum. The curved needle is dragged down the interatrial system into the fossa ovalis area of the septum. A ridge surrounds this region and provides a tactile and visual indication of falling into the fossa. The tube 11 is oriented 45° dorsally. The fluoroscopic display of the needle tip and the hub pointer on the needle assembly provide confirmation of proper orientation. When the needle is properly positioned, the needle wire 9 is advanced and the septum is pierced.

FIG. 6(b) shows the subsequent dilation of the septal hole as the catheter is advanced over the needle assembly. FIG. 6(c) shows the further dilation of the septal hole as the cannula enters the left atrium. The appearance of red oxygenated blood from the left atrium in the cannula indicates the tip of the cannula is in the left atrium. The fluoroscopic display provides an indication of the actual cannula location. As an option, the needle wire 9 can be removed from the metal tubes and a radio-opaque dye injected to further confirm the location of the cannula. Also, the curved end of the guide wire can be advanced and observed under fluoroscopy to determine the distance to the lateral left atrial wall. When the cannula is properly positioned, the guide wire, needle assembly and catheter are withdrawn and removed.

Figure 7:
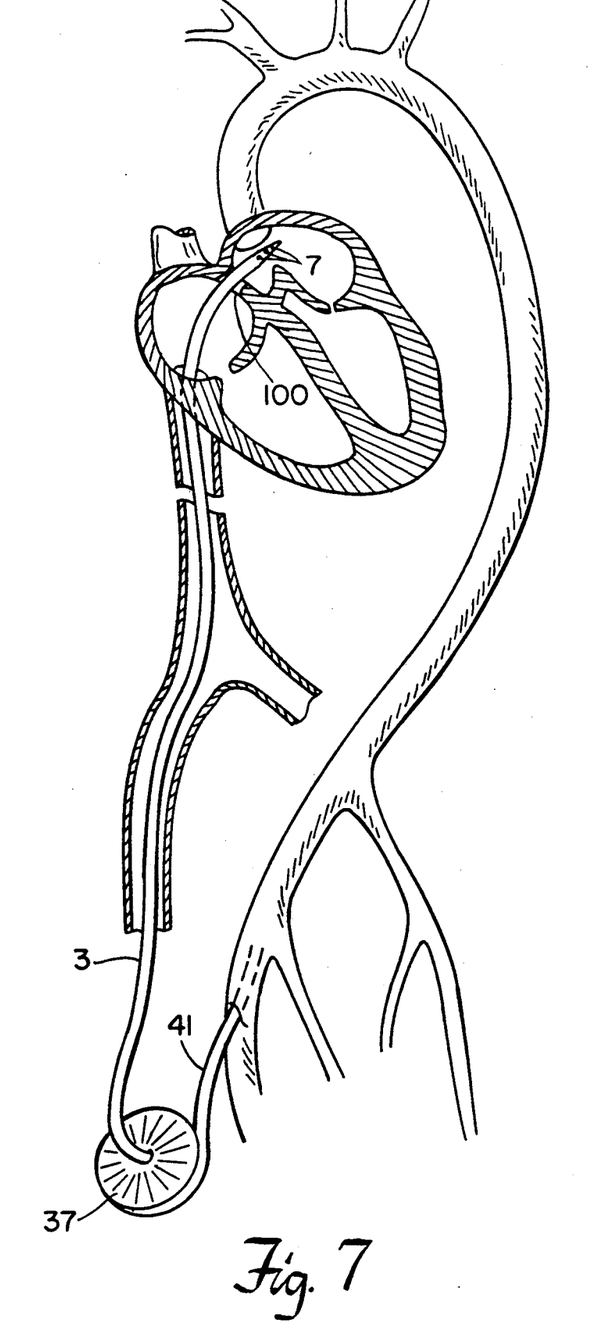
FIG. 7 provides a schematic view of the venous cannulation system, pump, and arterial cannula.

FIG. 7 shows the complete left ventricular assist system. Oxygenated blood from the left atrium drains through the venous cannula 3 to pump 37. A centrifugal pump which can pump blood safely for several days is shown. However, any conventional pump can be used. For example, a roller pump can also be used in the system. The blood is returned to the body by means of an arterial cannula 41 inserted into the femoral artery.

Possible clinical applications of the invention include three separate aspects of adult cardiac care. First, during coronary angioplasty, there is a risk of unexpected coronary artery damage resulting in hemodynamic collapse. If the patient was known to be high risk prior to the angioplasty procedure, a conventional guide wire could be positioned across the interatrial septum prior to the angioplasty. This device, with its guide wire removed, could then be inserted over the prepositioned guide wire for left ventricular assist if a significant problem developed during the procedure. If the problem was completely unanticipated, however, the percutaneous transseptal left atrial cannula atrial system would include all the elements necessary to achieve expeditious transseptal left atrial cannulation and facilitate left ventricular assist.

Secondly, in centers that have an active cardiac transplant program, many patients develop severe cardiac failure while waiting for a heart donor. Mild to moderate cardiac failure can be managed with medications and an intra-aortic balloon pump. However, severe cardiac failure requires some form of left ventricular assist. Although surgically implantable devices are available at a number of centers, arrangements for their insertion is often complex and involves many delays. A number of centers also do not have access to any implantable technology despite having an active cardiac transplant program. This invention would allow left atrial drainage without thoracotomy and the establishment of left ventricular assist using universally available centrifugal pumps while arrangements were made either for surgical insertion of a more permanent implantable device or while a donor heart was found.

Finally, this device could be considered for post-cardiotomy left ventricular assist by inserting the device in the operating room after heart surgery. In this setting, the patient may have failed to separate from the heart-lung machine and will require several days of temporary left ventricular assist. Insertion in this setting need not be under fluoroscopic control but could be directed by the surgeon through the groin to the heart. The needle assembly and catheter could be directed across the septum by feeling the cannula through the wall of the right atrium while still on cardiopulmonary bypass. The advantage of this approach over direct surgical cannulation of the heart would be that the chest would not have to be reopened several days later when the system was ready to be removed. The risk of bleeding around surgical cannulation sites would be eliminated and the risk of postoperative mediastinal infection would be reduced.

EQUIVALENTS

Those skilled in the art will recognize, or be able to ascertain, using no more than routine experimentation, many equivalents to the specific embodiments of the invention described herein.

These and all other equivalents are intended to be encompassed by the following claims.

We claim:

1. A cannulation system for draining blood from the left atrium of the heart through a blood vessel comprising, as an assembly to be inserted through the blood vessel:
    a catheter having a distal end and a proximal end, said distal end including an orifice and the catheter width being reduced near the orifice;
    a guide wire;
    a needle;
    said guide wire and said needle located axially in the catheter such that either the guide wire or the needle can alternately be extended through the orifice at the catheter distal end; and
    a cannula, having a distal end and a proximal end, surrounding the catheter, said cannula having a hole located at the extreme distal end of the cannula such that the hole of the cannula slides over the exterior of the catheter, the needle having a stiffness sufficient to serve as an obturator such that the catheter and cannula can be passed over the needle and through the atrial septum, but flexible enough to pass through a blood vessel.

2. A cannulation system as claimed in claim 1 wherein the needle has shape memory and the catheter and cannula are straight but for shape imparted by the needle.

3. A cannulation system for accessing blood in the left atrium through a blood vessel comprising, as an assembly to be inserted through the blood vessel:
- a catheter having a distal end and a proximal end and an axial cavity, said distal end including an orifice and the catheter width being reduced near the orifice;
- a guide wire;
- a needle;
- said guide wire and said needle located axially in the catheter such that either the guide wire or the needle can alternately be extended through the orifice at the catheter distal end; and
- a cannula, having a distal end and a proximal end, surrounding the catheter, said cannula having a hole located at the extreme distal end of the cannula such that the hole of the cannula slides over the exterior of the catheter.

4. A cannulation system, as recited in claim 3, further comprising:
- a plurality of holes on the side of said cannula;
- a peel-away sheath assembly including a thin-walled tube with a tapered end which causes the sheath to be retained in fixed portion on the cannula as the cannula is moved through subcutaneous tissue to cover the plurality of holes on the side of the cannula,
- said tube being scored such that it can be pulled back from the cannula and peeled away.

5. A cannulation system, as recited in claim 4, further comprising a hub which is molded onto the thin-walled tube.

6. A cannulation system, as recited in claim 5, in which the cannula is coated with an anti-thrombogenic coating.

7. A cannulation system, as recited in claim 6, in which the needle is sufficiently stiff to direct the catheter and then the cannula over the needle.

8. A cannulation system, as recited in claim 7, in which the guide wire has a curved flexible end such that the guide wire can guide the cannulation system in a blood vessel and the guide wire can be extended from the catheter orifice to assess the distance from the catheter orifice to a body part.

9. A cannulation system, as recited in claim 8, in which the needle further comprising an inner metal tube and an outer metal tube, such that the inner metal tube is longer and narrower than the outer metal tube and a molded hub which joins the inner and outer metal tubes coaxially, said inner metal tube has a distal end which is rounded to prevent scraping within the catheter, said inner metal tube can pass through the catheter orifice, said outer metal tube cannot pass through the catheter orifice such that the inner metal tube protrudes a fixed distance from the catheter orifice.

10. A cannulation system, as recited in claim 9, in which the distal end of the needle may be curved.

11. A cannulation system, as recited in claim 10, in which said inner and outer metal tubes have a proximal end, said needle proximal end further comprising a hub with a pointer such that the angular orientation of the pointer indicates the spatial orientation of the curved distal end of the needle.

12. A cannulation system, as recited in claim 11, in which said needle further comprising a needle wire with a distal end and a proximal end, and a molded hub attached to the needle wire proximal end, said needle wire is positioned within the inner metal tube such that movement of the molded hub towards the catheter distal end advances the needle wire distal end through the inner metal tube distal end.

13. A cannulation system, as recited in claim 3, in which the cannula is coated with an anti-thrombogenic coating.

14. A cannulation system, as recited in claim 3, in which the needle is sufficiently stiff to permit the catheter and cannula to advance through the atrial septum over the needle assembly.

15. A cannulation system, as recited in claim 14, further comprising a guide wire and needle length which are long enough to allow a substantial length to extend out of the body at the groin for manipulation even when the distal ends of the guide wire and needle are positioned in the heart.

16. A cannulation system, as recited in claim 3, in which the guide wire has a curved flexible end such that the guide wire can guide the cannulation system in a vein and the guide wire can be extended from the catheter orifice to assess the distance from the catheter orifice to the left atrial wall.

17. A cannulation system, as recited in claim 16, in which the guide wire is further comprised of a core wire and a stainless steel spring wire such that said spring wire is wrapped around said core wire.

18. A cannulation system, as recited in claim 3, further comprising a guide wire and needle length which are long enough to allow a substantial length to extend out of the body at the groin for manipulation even when the distal ends of the guide wire and needle are positioned in the heart.

19. A cannulation system, as recited in claim 3, in which the needle further comprises a metal tube with a narrowed distal end such that a predetermined length of tube can extend out of the catheter orifice but a thicker tube width is stopped at the orifice.

20. A cannulation system, as recited in claim 19, in which the tube further comprises an inner metal tube and an outer metal tube, such that the inner metal tube is longer and narrower than the outer metal tube and a molded hub which joins the inner and outer metal tubes coaxially, said inner metal tube having a distal end which is rounded to prevent scraping within the catheter, said inner metal tube being of a diameter to pass through the catheter orifice, said outer metal tube being of a diameter such that it cannot pass through the catheter orifice such that the inner metal tube cannot protrude beyond a fixed distance from the catheter orifice.

21. A cannulation system, as recited in claim 20, in which the distal end of the needle may be preformed to a curve by the operator.

22. A cannulation system, as recited in claim 21, in which said inner and outer metal tubes have a proximal end, said metal tube proximal end further comprising a hub with a pointer such that the angular orientation of the pointer indicates the spatial orientation of the curved distal end of the needle.

23. A cannulation system, as recited in claim 20, in which said transseptal needle further comprises a needle wire with a distal end and a proximal end, and a hub attached to the needle wire proximal end, said needle wire being positioned within the inner metal tube such that movement of the molded hub towards the catheter distal end extends the needle wire distal end through the tube distal end a fixed short distance.

24. A cannulation system, as recited in claim 3, further comprising:

a flexible, hollow cannula hub with a distal end and a proximal end;

said cannula hub distal end being clampable such that blood in the cannula will not pass through the cannula hub proximal end.

25. A cannulation system, as recited in claim 24, further comprising:

a hollow reducer plug with a distal end and a proximal end;

said reducer plug distal end being connected to said cannula hub proximal end; and said reducer plug proximal end surrounding said catheter proximal end, the interior diameter of the reducer plug being smaller than the interior diameter of the cannula hub.

26. A cannulation system, as recited in claim 25, in which the catheter proximal end further comprises:

a male connector with a distal end and a proximal end, said male connector distal end being coupled to said reducer plug proximal end;

a dual lumen elastic bushing which is positioned in the male connector proximal end; said bushing holding the guide wire and the needle, said male connector proximal end including a holder for the bushing; and a closing ring positioned at the male connector proximal end such that a friction fit prevents the guide wire and the needle from moving in the catheter axially if desired.

27. A cannulation system as claimed in claim 3 wherein the needle comprises a tube and a needle wire within the tube which may be extended beyond the tip of the tube or retracted within the tube.

28. A cannulation system as claimed in claim 3 wherein the needle has shape memory and the catheter and cannula are straight but for shape imparted by the needle.

29. A cannula peel-away sheath assembly comprising:

a cannula including a plurality of holes located on the side of the cannula parallel to the longitudinal axis of the cannula; and a peel-away sheath assembly including a thin-walled tube with a tapered end which causes the sheath to be retained in fixed position on the cannula as the cannula is moved through subcutaneous tissue to cover the plurality of holes on the side of the cannula, such that the sheath assembly prevents the cannula holes from accumulating fat particle debris when passing through subcutaneous fat prior to reaching a blood vessel; and said tube is scored such that the sheath assembly can be pulled back and peeled away after the cannula is within the blood vessel.

30. An apparatus, as recited in claim 29, further comprising a hub coupled to a proximal end of the tube.

31. A cannulation system for draining blood from the left atrium of the heart through a blood vessel as an assembly to be inserted through the blood vessel:

a catheter having a distal end and a proximal end, said distal end including an orifice and the catheter width being reduced near the orifice;

a guide wire;

a needle;

said guide wire and said needle located axially in the catheter such that either the guide wire or the needle can alternately be extended through the orifice at the catheter distal end;

a cannula, having a distal end and a proximal end, surrounding the catheter, said cannula having a hole located at the extreme distal end of the cannula such that the hole of the cannula rides over the exterior of the catheter;

said needle is sufficiently stiff to direct the catheter and then the cannula over the needle;

a peel-away sheath assembly including a thin-walled tube with a tapered end which causes the sheath to be retained in fixed portion on the cannula as the cannula is moved through subcutaneous tissue to cover the plurality of holes on the side of the cannula;

said thin-walled tube being scored such that it can be pulled back from the cannula and peeled away;

the guide wire has a curved flexible end such that the guide wire can guide the cannulation system in a blood vessel and the guide wire can be advanced from the catheter orifice to assess the distance from the catheter orifice to a body part; and a needle with a narrowed distal end such that a predetermined length of needle can extend out of the catheter orifice but a thicker needle width is stopped at the orifice.

32. A cannulation system as claimed in claim 31 wherein the needle comprises a tube and a needle wire within the tube which may be extended beyond the tip of the tube or retracted within the tube.

33. A cannulation system as claimed in claim 31 wherein the needle has shape memory and the catheter and cannula are straight but for shape imparted by the needle.

34. A percutaneous transseptal left atrial cannulation system for draining oxygenated blood from the left atrium of the heart through a venous cannula and returning the blood to the body through an arterial cannula after passing through an extra-corporeal pump, said venous cannulation system comprising:

a catheter having a distal end and a proximal end, said distal end including an orifice and the catheter width being reduced near the orifice;

a guide wire;

a needle;

said guide wire and said needle being located axially in the catheter such that either the guide wire or the needle can be alternately advanced through the orifice at the catheter distal end, said needle having a distal end which may be curved; and a cannula having a distal end and a proximal end, said cannula distal end including a plurality of holes located on the side of the cannula parallel to the longitudinal axis of the cannula and an end hole located at the extreme distal of the cannula; said end hole of the cannula rides over the exterior of the catheter; said needle is sufficiently stiff to serve as an obturator to direct the catheter and then the cannula over the needle;

such that said venous cannulation system is adapted to enter the femoral vein, pass up the inferior vena cava, enter the right atrium, position the needle assembly distal end at the septum, pierce the septum to form a hole in the septum and to position the needle assembly distal end in the left atrium, move the catheter over the needle assembly to further dilate the septal hole, move the cannula into the left atrium to further dilate the septal hole, and remove the needle, the guide wire, and the catheter from the cannula to permit flow of oxygenated blood from the left atrium to the extra-corporeal pump and through the arterial cannula back to the body.

35. A method of percutaneous transseptal left atrial ventricular assist for extracting oxygenated flood from the left atrium of the heart by a venous cannulation system and returning the blood to the body by an arterial cannula after passing through an extra-corporeal pump comprising the steps of:
   (a) inserting the venous cannulation system into the femoral vein, said venous cannulation system including a guide wire and a needle located in a catheter with a distal end orifice and a cannula riding over the exterior of the catheter;
   (b) advancing the guide wire through the catheter orifice and moving the catheter over the guide wire through the inferior vena cava to the septum in the right atrium of the heart;
   (c) withdrawing the guide wire into the catheter and extending the needle distal end to the septum;
   (d) piercing the septum with the needle to form a hole;
   (e) moving the catheter over the needle assembly to further dilate the septal hole;
   (f) moving the cannula into the left atrium to further dilate the septal hole;
   (g) withdrawing the guide wire, the needle, and the catheter from the cannula; and
   (h) draining oxygenated blood from the left atrium through the venous cannula to the extra-corporeal pump and back to the body through the arterial cannula.

36. A method, as recited in claim 35, in which the cannula distal end comprises a plurality of holes located on its side parallel to the longitudinal axis of the cannula, the method comprising covering the cannula holes with a peel-away sheath during the initial step of inserting the venous cannula into the femoral vein such that the sheath prevents the cannula holes from accumulating fat particle debris prior to reaching the blood stream and peeling away the sheath after the cannula is within the femoral vein.

37. A method, as recited in claim 35, in which the needle further comprises a tube with a narrowed distal end such that predetermined length of tube can extend out of catheter orifice.

38. A method, as recited in claim 37, in which the tube further comprises:
   an inner metal tube and an outer metal tube, such that the inner metal tube is longer and narrower than the outer metal tube and a molded hub which joins the inner and outer metal tubes coaxially, said inner metal tube has a distal end which is rounded to prevent scraping within the catheter, said inner metal tube can pass through the catheter orifice, said outer metal tube cannot pass through the catheter orifice such that the inner metal tube protrudes a fixed distance from the catheter orifice.

39. A method, as recited in claim 38, in which the distal end of the needle may be curved.

40. A method, as recited in claim 39, in which said inner metal tube has a proximal end, said inner metal proximal end further comprising a hub with a pointer such that the angular orientation of the pointer indicates the spatial orientation of the curved distal end of the needle.

41. A method, as recited in claim 38, in which said transseptal needle assembly further comprises a needle wire with a distal end and a proximal end, and a hub attached to the needle wire proximal end, said needle wire being positioned within the inner metal tube such that movement of the molded hub towards the catheter distal end advances the needle wire distal end through the inner metal tube distal end.

42. A method of inserting a cannula into a blood vessel, said cannula including a plurality of holes located on the side of the cannula parallel to the longitudinal axis of the cannula, comprising the steps of:
   (a) attaching a peel-away sheath assembly to the cannula to cover the cannula holes, said peel-away sheath assembly including a thin-walled tube, said tube is scored;
   (b) inserting the cannula peel-away sheath assembly into a blood vessel by passing through a subcutaneous layer of fat such that said sheath assembly prevents the cannula holes from accumulating fat particle debris; and
   (c) pulling back and peeling away the sheath assembly after the cannula is within the blood vessel.

* * * * *

UNITED STATES PATENT AND TRADEMARK OFFICE
CERTIFICATE OF CORRECTION

PATENT NO. : 5,190,528
DATED : March 2, 1993
INVENTOR(S) : James D. Fonger et al.

It is certified that error appears in the above-identified patent and that said Letters Patent is hereby corrected as shown below:

In Claim 9, column 9, line 46, change "comprising" to
---comprises---.

In Claim 12, column 9, line 65, change "comprising" to
---comprises---.

In Claim 34, column 12, line 53, after the word "distal" insert ---end---.

Signed and Sealed this

First Day of February, 1994

*Attest:*

BRUCE LEHMAN

*Attesting Officer*  *Commissioner of Patents and Trademarks*